United States Patent [19]

Fox et al.

[11] Patent Number: 4,504,684

[45] Date of Patent: Mar. 12, 1985

[54] METAL COORDINATION POLYMERS AS HYDROFORMYLATION AND HYDROGENATION CATALYSTS

[75] Inventors: Joseph R. Fox, Solon; Frederick A. Pesa, Aurora, both of Ohio

[73] Assignee: The Standard Oil Company, Cleveland, Ohio

[21] Appl. No.: 520,084

[22] Filed: Aug. 4, 1983

Related U.S. Application Data

[63] Continuation of Ser. No. 337,559, Jan. 6, 1982, abandoned.

[51] Int. Cl.$^3$ ............................................. C07C 45/50
[52] U.S. Cl. ........................................ 568/454; 568/909
[58] Field of Search ............................ 568/909, 454

[56] References Cited

U.S. PATENT DOCUMENTS

| | | | |
|---|---|---|---|
| 3,644,563 | 2/1972 | Bauer | 568/454 |
| 3,689,533 | 9/1972 | Schutz | 260/488 |
| 3,787,459 | 1/1974 | Frankel | 568/454 |
| 4,012,450 | 3/1977 | Bond | 568/454 |
| 4,193,942 | 3/1980 | Gerritsen et al. | 568/454 |
| 4,276,195 | 6/1981 | Verkade | 252/431 |

*Primary Examiner*—Werren B. Lone
*Attorney, Agent, or Firm*—Teresan W. Gilbert; Joseph G. Curatolo; Larry W. Evans

[57] ABSTRACT

Solid catalysts comprising a solid inorganic catalyst support material and polymeric transition metal complex are ideally suited for use as solid catalysts in various vapor phase heterogeneous continuous reactions.

4 Claims, No Drawings

METAL COORDINATION POLYMERS AS HYDROFORMYLATION AND HYDROGENATION CATALYSTS

CROSS REFERENCE TO RELATED APPLICATION

This application is a continuation of application Ser. No. 337,559 filed Jan. 6, 1982 which is now abandoned.

BACKGROUND OF THE INVENTION

The present invention relates to a novel vapor phase process and a catalyst useful therefore.

Many catalytic processes employing transition metal complex catalysts are known. Such processes are almost always carried out in batch operation in liquid phase under pressure with the transition metal complex catalyst being dissolved in the liquid reaction medium. When the reaction is completed, the expensive transition metal complex catalyst if it is to be reused, must be separated from the reaction system. Because the catalyst is dissolved in the liquid phase reaction system, this is difficult.

U.S. Pat. No. 4,276,195 to Verkade discloses a technique for overcoming this disadvantage. In accordance with this technique, transition metal complex catalysts are formulated in the form of polymers comprising repeating groups of the transition metal and a suitable bidentate ligand. The transition metal actually forms a part of the polymer chain and hence is firmly bonded into the polymer system. The polymer has a high enough molecular weight so that it is in solid form and exhibits little solubility in the liquid reaction system. Accordingly, the polymer catalyst can be easily removed from the reaction system by filtration or other simple physical separation.

Although use of the Verkade catalysts will reduce or eliminate a number of problems associated with liquid phase batch operations, they nonetheless appear suitable for use only with liquid phase processes. Furthermore, it has been found that these polymers will, over time, at least partially dissolve in the liquid reaction medium, which significantly reduces the advantages of these materials.

Accordingly, it is an object of the present invention to provide a new solid phase catalyst which is based on a transition metal complex as the active catalytic material and which is ideally suited for use in vapor phase heterogeneous continuous reactions.

SUMMARY OF THE INVENTION

This and other objects are accomplished by the present invention which is based on the discovery that solid catalysts comprising a solid inorganic catalyst support material and a polymeric transition metal complex are ideally suited for use as solid catalysts in various vapor phase heterogeneous continuous reactions.

Thus, the present invention provides a novel solid catalyst for catalyzing the vapor phase reaction of various vapor phase reactants to form desired vapor phase products, the catalyst comprising (a) a solid inorganic catalyst support material and (b) a solid active catalytic material comprising a polymeric transition metal complex capable of catalyzing the reaction.

In addition, the present invention provides an improvement in known catalytic processes for converting organic reactants to products wherein the reactants are contacted with catalysts comprising polymeric transition metal complexes to form the desired products, the improvement in accordance with the present invention wherein the reactants are in the vapor phase when contacted with the catalysts and further wherein the catalysts comprise (a) solid inorganic catalyst support materials and (b) solid active catalytic materials comprising polymeric transition metal complexes capable of catalyzing the reactions.

DETAILED DESCRIPTION

Reactions

The present invention relates to an improvement over known processes wherein organic reactants are converted to products by contact with polymeric transition metal complexes. The invention is applicable to any catalytic process in which (1) the reactant is an organic compound, (2) the organic compound is catalytically reactable to form a desired product by contact with a polymeric transition metal complex, (3) the organic reactant can exist in the vapor phase under conditions which neither deactivate nor destroy the polymeric transition metal complex catalyst and (4) the desired products also exist in the vapor phase under conditions in which the polymeric transition metal catalyst and the reactants are not destroyed.

Such reactions are well known and described, for non-vapor phase reactants, in the aforementioned Verkade U.S. Pat. No. 4,276,195, the disclosure of which is incorporated herein by reference. Examples of such reactions are the hydrogenation of olefins to product paraffins, the isomerization of olefins, the hydrocyanation of diolefins to produce dicyano compounds, the hydroformylation of olefins to produce aldehydes, the carbonylation of alcohols to produce acids, the hydrosilylation of olefins to produce organosilanes and the metathesis of olefins.

Reactions of a particular interest are the hydroformylation of olefins to produce aldehydes. Normally, the olefin will have no more than 10 carbon atoms.

The invention process is a vapor phase heterogeneous continuous reaction. In other words, the reaction is carried out in a reaction zone in which is located a solid bed of catalyst, either in fixed-bed or fluid-bed form. Reactants in the vapor phase are continuously contacted with the bed of solid catalyst and products of the reaction in the vapor phase are continuously withdrawn from the catalyst bed.

The pressure and temperature of the reaction system are not critical. Of course, they must be selected so that the process is a vapor phase heterogeneous reaction.

Catalyst

The catalysts of the present invention are solid materials which comprise (a) a solid, inorganic catalyst support material and (b) a solid, active catalytic material comprising a polymeric transition metal complex capable of catalyzing the reaction of interest.

Solid, inorganic catalyst support materials are well known in the art and used in many solid catalysts. Examples of such materials are silica, alumina, Alundum, zirconia, titania, magnesia, zeolites, elemental carbon and various naturally occuring clays such as kiesulguhr and montmorillonite. Such materials can be in both fixed-bed and fluid-bed form and can be porous or nonporous. Such materials are normally inert to the reaction of interest, but may exhibit some type of effect in a particular reaction.

The active catalytic material in the inventive catalyst is composed of a polymeric transition metal complex which is capable of catalyzing the reaction of interest. Such materials are well known and described, for example, in the above noted Verkade patent. They are polymeric materials which are composed of polymerized repeating groups, the groups being composed of a transition metal and a polydentate, non-chelating ligand. Generally, metals of Group IVB, VB, VIB, VIIB, VIII and IB of the Periodic Table are used as the transition metals. Specific examples are titanium, vanadium, chromium, manganese, iron, cobalt, nickel, zinc, zirconium, molybdenum, ruthenium, rhodium, palladium, tantalum, osmium and iridium. Preferred are iron, rhodium, nickel, molybdenum, cobalt, palladium and titanium.

The polydentate ligands as indicated in the Verkade patent are those which mimic monodentate ligands of known transition metal complex catalysts having catalytic activity for the reactions in question. Examples of such polyfunctional ligands are shown in the table in the Verkade patent. In accordance with the invention, it has been further found that the polyfunctional non-chelating ligand need not mimic ligands on the corresponding homogeneous transition metal complex catalyst, it being sufficient that the polyfunctional ligand be non-chelating and not contain substituents which would interfere with the reaction of interest.

As indicated above, the present invention finds particular applicability to the hydroformylation of olefins to produce aldehydes. In this reaction, polymeric transition metal complex catalysts which are particularly appropriate can be defined by the following formula:

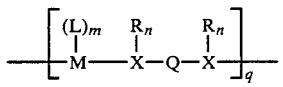

wherein
M is Co, Rh or Ir, preferably Rh,
L is Cl, F, Br, I, H, CO or mixtures thereof, preferably CO and one of H and Cl,
X is S, N, P, As, Sb or Bi, preferably As or P,
R is an alkyl or aryl group having no more than 12 carbon atoms, preferably phenyl,
Q is an organic moiety preferably having no more than 20 carbon atoms, preferably para-phenyl, meta-phenyl, acetylyl and trans-ethenyl, and
wherein
m is 2 or 3
n is 2 except when X is S in which case n is 1, and
q is greater than 2

Particularly preferred polymeric transition metal complex catalysts for use in the hydroformylation of olefins to produce aldehydes are those defined by the formula:

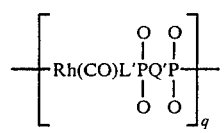

wherein
L' is H or Cl,
Q' is para-phenyl, trans-ethenyl or acetylyl, and
q is greater than 3.

The inorganic catalyst support material and the polymeric transition metal complex can be combined in the inventive catalyst in essentially any form. For example, when the catalyst is in the form of an agglomerate, the complex and the support can be present in the agglomerate as a physical mixture of discrete coherent particles. Also, the polymeric transition metal complex can be present as a coating on the outside surfaces of discrete pellets or agglomerates of the catalyst support material. In addition, if the catalyst support material is porous, the polymeric transition metal complex can be present as a coating on the pore surfaces of the pores.

The amount of polymeric transition metal complex in the inventive catalyst is not critical. Most conveniently, the polymeric transition metal complex should be present in an amount of 1 to 50%, preferably 5 to 30%, more preferably 5 to 10%, measured as the transition metal and based on the weight of the catalyst particle as a whole.

The catalysts of the invention can be made by any conventional catalyst forming technique. For example, when the inorganic catalyst support material is silica, a particularly convenient way of making the catalyst is to form an aqueous slurry of the polymeric transition metal complex and silica in water by mixing a conventional silica sol and the polymeric transition metal complex in powder form and then evaporating the water from the slurry under moderate heat. Evaporation of the water causes the silica to condense to form discrete agglomerates of silica particles bonded to one another incorporating therein discrete particles of the powdery polymeric transition metal complex.

If a coated catalyst is desired, the catalyst can be made by gently agitating a mixture of the powdery polymeric transition metal complex and the inorganic catalyst support material after the surfaces of the inorganic catalyst support material have first been wet with water. This technique is more thoroughly described in U.S. Pat. No. 4,077,912 (Dohlyj patent), the disclosure of which is incorporated herein by reference.

Still another technique for making catalyst in accordance with the present invention is to form the polymeric transition metal complex in situ in the pores of a porous inorganic catalyst support material. This can be done by carrying out the exchange reaction described in the above noted Verkade patent in the liquid phase with the inorganic catalyst support material being slurried in the liquid medium. Alternately, the bidentate ligand and the transition metal, preferably in the form of a chloride (e.g. $RhCl_3 \cdot 3H_2O$ or $[RhCl(CO)_2]_2$) can be slurried in a suitable solvent in which the inorganic catalyst support material is also slurried. Specific details of catalyst preparation are illustrated in the following working examples.

In order to more thoroughly demonstrate the present invention, the following working examples are presented.

EXAMPLE 1

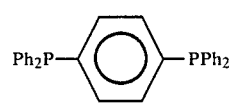

(2.1 g, 4.7 mmol) was dissolved in $CH_2Cl_2$ (100 ml) in a 250 ml 3-neck flask equipped with a reflux condenser. After the solution was stirred under $N_2$ for 1 hour,

[RhCl(CO)₂]₂ (0.183 g, 0.47 mmol) was added as a solid. The solution was brought to reflux and allowed to react for 30 min. During this time, a yellow solid was formed which precipitated from solution. The yellow solid was collected on a fine frit, washed with CH₂Cl₂, dried and weighed 0.551 g. The theoretical yield of polymeric

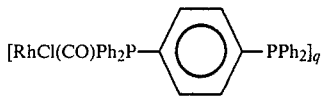

is 0.577 g (yield=95%). The yellow solid is air stable and is insoluble in hot CH₂Cl₂, hot CHCl₃, toluene, benzene, DMSO and DMF.

EXAMPLE 2

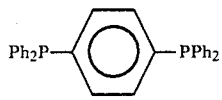

(0.34 g, 0.76 mmol) was dissolved in CH₂Cl₂ (30 ml) in a 100 ml 3-neck flask equipped with a reflux condenser and a dropping funnel which contained RhCl₃.3H₂O (0.05 g, 0.19 mmol) dissolved in absolute ethanol (10 ml). The phosphine solution was brought to reflux under N₂ and the RhCl₃ solution was added dropwise, followed by the addition of aqueous formaldehyde (5 ml). The solution was allowed to reflux for 45 min., but no color change indicative of a reaction was observed. The N₂ was replaced by a CO purge and immediately the red soltuion began to lighten and yellow solid began to precipitate from solution. The reaction was allowed to proceed for 45 min., after which time the yellow solid was collected on a fine frit, washed and dried. The yield of polymeric

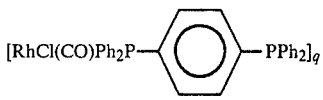

was 0.106 g (91%).

EXAMPLE 3

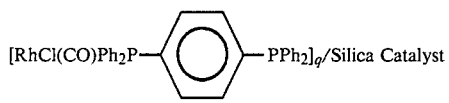

0.5 g of the polymeric rhodium complex was synthesized by the method of in Example 1 above and mixed with 12.5 g of a 40 wt % silica sol (Nalco 2327). The water in the sol was then boiled off and the resultant solid dried in an oven at 110° C. for 30 minutes. A catalyst particulate containing 1.5% rhodium, measured as rhodium metal and based on the entire weight of the catalyst, was obtained.

EXAMPLE 4

Vapor Phase Hydroformylation of Propylene

The above catalyst was loaded into a 40 cc stainless steel fixed-bed reactor. A feed comprising 3 CO/3 H₂/1 propylene was continuously fed to the the fixed-bed reactor at a rate such that the hydrogen flow rate was 369 cc/min. The reaction temperature was 200° C. and the reaction pressure was 1100 psi. The gross reaction product was recovered and analyzed by gas chromatography. It was found that the propylene conversion was 11.7% and selectivity to the different products were as follows: 35.3% isobutyraldehyde, 60.6% n-butyraldehyde, 0.06% isobutanol and 0.6% n-butanol.

Although only a few embodiments of the invention have been illustrated above, it should be appreciated that many modifications can be made without departing from the spirit and scope of the invention. All such modifications are intended to be included within the scope of the present invention, which is to be limited only by the following claims:

We claim:

1. A hydroformylation process for converting an olefin to the corresponding aldehyde by a reaction wherein said olefin with hydrogen and carbon monoxide is contacted with a catalyst comprising a polymeric transition metal complex to form said aldehyde, the improvement wherein said olefin is in the vapor phase when contacted with said catalyst, said aldehyde is in the vapor phase when withdrawn from said catalyst and said catalyst comprises (a) a solid, inorganic catalyst support material and (b) a solid, active catalytic material comprising a polymeric transition metal complex capable of catalyzing said reaction.

2. The process of claim 1 wherein said reactant is an olefin having no more than 10 carbon atoms and further wherein said polymeric transition metal complex is capable of catalyzing the hydroformylation of said olefin to the corresponding aldehyde.

3. The process of claim 2 wherein said catalyst is defined by the formula:

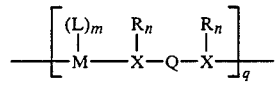

wherein

M is Co, Rh or Ir,

L is Cl, F, Br, I, H, CO or mixtures thereof,

X is S, N, P, As, Sb or Bi,

R is an alkyl or aryl group having no more than 12 carbon atoms,

Q is an organic moiety, and wherein m is 2 or 3 n is 2 except when X is S in which case n is 1, and q is greater than 2

4. The process of claim 3 wherein said polymeric transition metal complex is defined by the formula:

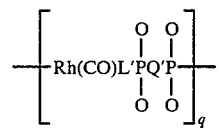

wherein

L' is H or Cl,

Q' is para-phenyl, trans-ethenyl or acetylyl, and q is greater than 3.

* * * * *